United States Patent
Rynerson et al.

(10) Patent No.: US 10,548,694 B2
(45) Date of Patent: Feb. 4, 2020

(54) METHOD AND SYSTEM FOR PROCESSING DENTAL PROSTHESES

(71) Applicant: DENTAL WINGS INC., Montréal (CA)

(72) Inventors: Michael Landry Rynerson, Montréal (CA); Pierre-Olivier Roy, Québec (CA); Jean-Marc Perot, Mont-Royal (CA); Robin Provost, Montréal (CA)

(73) Assignee: DENTAL WINGS INC. (CA)

( * ) Notice: Subject to any disclaimer, the term of this patent is extended or adjusted under 35 U.S.C. 154(b) by 74 days.

(21) Appl. No.: 15/517,760

(22) PCT Filed: Oct. 9, 2015

(86) PCT No.: PCT/CA2015/051025
§ 371 (c)(1),
(2) Date: Apr. 7, 2017

(87) PCT Pub. No.: WO2016/054744
PCT Pub. Date: Apr. 14, 2016

(65) Prior Publication Data
US 2017/0245969 A1    Aug. 31, 2017

Related U.S. Application Data

(60) Provisional application No. 62/061,803, filed on Oct. 9, 2014.

(51) Int. Cl.
*G06F 19/00* (2018.01)
*A61C 9/00* (2006.01)
(Continued)

(52) U.S. Cl.
CPC .............. *A61C 9/0086* (2013.01); *A61B 1/24* (2013.01); *A61B 6/14* (2013.01); *A61C 5/20* (2017.02);
(Continued)

(58) Field of Classification Search
CPC ............ A61C 13/0004; A61C 13/0022; A61C 13/082; A61C 13/0006; A61C 9/0053;
(Continued)

(56) References Cited

U.S. PATENT DOCUMENTS 6,136,132 A * 10/2000 Kinzie .................... B32B 38/10
156/258
6,193,923 B1 * 2/2001 Leyden ................... B29C 41/12
264/401
(Continued)

OTHER PUBLICATIONS

B. Tholt, W. G. Miranda-Júnior, R. Prioli, J. Thompson, and M. Oda (2006) Surface Roughness in Ceramics with Different Finishing Techniques Using Atomic Force Microscope and Profilometer. Operative Dentistry: Jul. 2006, vol. 31, No. 4, pp. 442-449. (Year: 2006).*
(Continued)

*Primary Examiner* — Michael D Masinick
(74) *Attorney, Agent, or Firm* — Lavery, De Billy, LLP; Hugh Mansfield (57) ABSTRACT

A system and method for optimising the preparation of dental restorations is provided. The system comprises a dental restoration surface processing unit, a dental restoration assessment unit, a database comprising a treatment parameters database and a processing protocols database, a processor operationally coupled to said dental restoration surface processing unit and a protocol selector. The method treats a dental restoration surface using the system and according to one or more selected processing protocol.

32 Claims, 8 Drawing Sheets

(51) Int. Cl.
*A61C 5/77* (2017.01)
*A61C 5/20* (2017.01)
*A61B 1/24* (2006.01)
*A61B 6/14* (2006.01)
*A61C 8/00* (2006.01)
*A61C 13/00* (2006.01)
*A61C 13/08* (2006.01)

(52) U.S. Cl.
CPC .............. *A61C 5/77* (2017.02); *A61C 8/0048* (2013.01); *A61C 9/0053* (2013.01); *A61C 13/0004* (2013.01); *A61C 13/0018* (2013.01); *A61C 13/082* (2013.01)

(58) Field of Classification Search
CPC .............. A61C 13/0013; A61C 9/0046; A61C 13/0019
See application file for complete search history.

(56) References Cited

U.S. PATENT DOCUMENTS

| | | | | |
|---|---|---|---|---|
| 8,837,026 B2* | 9/2014 | Fisker | ..................... | G06T 17/00 345/420 |
| 10,123,706 B2* | 11/2018 | Elbaz | ........................ | G06T 7/75 |
| 2003/0222366 A1* | 12/2003 | Stangel | .............. | A61C 13/0004 264/16 |
| 2009/0088858 A1* | 4/2009 | Zinger | ................. | A61F 2/30767 623/18.11 |
| 2009/0142732 A1* | 6/2009 | Kahdemann | ......... | A61C 8/0069 433/174 |
| 2010/0042241 A1* | 2/2010 | Inoue | ................... | A61C 13/0004 700/97 |
| 2010/0310786 A1* | 12/2010 | Dunne | ................ | A61C 13/0004 427/487 |
| 2012/0015318 A1* | 1/2012 | Kasenbacher | ....... | A61C 1/0046 433/29 |
| 2012/0095732 A1 | 4/2012 | Fisker et al. | | |
| 2012/0219930 A1* | 8/2012 | Heinz | ..................... | A61C 3/02 433/215 |
| 2013/0056892 A1* | 3/2013 | Johnson | ............ | A61C 13/0013 264/19 |
| 2015/0057675 A1* | 2/2015 | Akeel | .................... | G16H 50/50 606/130 |

OTHER PUBLICATIONS

International Search Report of corresponding application PCT/CA2015/051025.

* cited by examiner

FIG-7

METHOD AND SYSTEM FOR PROCESSING DENTAL PROSTHESES

CROSS REFERENCE TO RELATED APPLICATIONS

This application claims benefit, under 35 U.S.C. § 119(e) of U.S. provisional application Ser. No. 62/061,803, filed on Oct. 9, 2014 which is incorporated herein in its entirety by reference.

TECHNICAL FIELD

This invention relates generally to an apparatus and methods to produce dental restorations. More specifically, this invention relates to apparatuses and methods for post-processing of dental prostheses.

BACKGROUND

Dental prostheses are commonly used in the repair of tooth damage that does not lend itself to simple fillings. Dental restoration presents many challenges. The tooth replacement or restoration material must conform as much as possible to the original function, shape, color, and texture of the tooth to be repaired or replaced. In particular post-processing steps such as finishing and polishing of dental restorations are important in any restorative procedure and can impact the aesthetics and longevity of the prosthesis. Improper post-processing can result in undesirable surface roughness or smoothness with impacts on such clinical outcome as plaque formation, gingival inflammation, and poor aesthetics.

The techniques used in dental restoration have evolved considerably over the past few decades. Traditional manual fabrication, which involves the acquisition of teeth impressions that are used by a technician to fabricate the dental restoration, is time consuming and of limited scope for finishing the final product. For example surface finish roughness of mechanically milled restorations often does not meet aesthetic and clinical requirement and requires manual polishing or glazing steps. Localized coloration and translucence needs to be adjusted manually by applying coloured glaze and stains. These additional materials may have limited durability and the post processing is time consuming.

More recent technologies such as computer assisted design/computer assisted manufacturing (CAD/CAM) systems offer more flexibility, precision and are less time consuming. However these systems also have limitations. In particular the current technologies are not optimized for the post-processing of the prosthesis to achieve superior appearance and texture. For example Selective Laser Sintering and Selective Laser Melting, two examples of layered additive manufacturing processes used in automated restoration production can result in the distortion in the underlying dental material due contraction/expansion of the material as a result of the thermal gradient generated by the thermo-physical process. In fact laser treatments of dental material disclosed have not been successful in providing a finished surface with adequate properties. Likewise conventional Computer Numerical Control (CNC) milling processes, which represents the most common automated process for dental prosthetic production, can also leave undesirable surface effects that must be removed by manual polishing.

In order to optimize such processes, complex processing algorithms are typically elaborated based on empirical data and theoretical simulations. However such automated methods are limited in their flexibility to adapt to particular conditions and design needs. There is therefore a need for improved systems and methods to reduce the time, cost, and variability in creating dental prostheses with acceptable surface characteristics with little or no manual effort.

SUMMARY OF THE INVENTION

The invention relates to apparatuses and methods for post processing of automatically produced dental restorations that provide improved final shade, surface finish, accuracy, resolution, and texture.

In one aspect of the invention there is provided a system for processing a dental restoration surface comprising: a dental restoration surface processing unit; a dental restoration assessment unit; a database comprising processing parameters database and a processing protocols database; a process or operationally coupled to the dental restoration surface processing unit to execute a processing of the dental restoration surface based on the one or more processing protocol; and a protocol selector configured to identify a processing protocol based on treatment parameters.

In another aspect of the invention there is provided a method for (post-) processing of a dental restoration surface comprising: providing a dental restoration surface to be treated according to one or more selected processing protocol; providing a dental restoration system comprising a dental restoration surface processing unit; a dental restoration assessment unit; a database comprising a treatment parameters database and a processing protocols database, a processor operationally coupled to the dental restoration surface processing unit and a protocol selector; and executing the processing of the dental restoration surface based on the one or more selected processing protocol.

In yet a further aspect of the invention there is provided a method for processing a dental material wherein the processing is laser, electron beam, ultrasonic, or other non-contact processing of a dental restoration material and wherein the processing protocols comprise instructions for treating a surface area of the material with a plurality of energy pulses (laser, electron beam, ultrasonic, or other non-contact method), each of the pulse having a focal spot area less than that of the total surface area to be treated, and each pulse having a predetermined overlapping area with at least one previously applied pulse.

BRIEF DESCRIPTION OF THE DRAWINGS

The invention will be better understood by way of the following detailed description of embodiments of the invention with reference to the appended drawings, in which.

DETAILED DESCRIPTION OF THE ILLUSTRATIVE EMBODIMENT

In the following description by surface or dental restoration surface it is meant the outer or inner surface of a dental prosthesis finished or being processed and the surface may comprise a certain volume of underlying bulk of material.

In one embodiment there is provided a system for making finished dental restoration prostheses. In particular there is provided a system for the production (treatment/modification) of dental prostheses particularly designed to produce finished prostheses with desired surface characteristics and properties. The system enables the digitized treatment of the surface of the dental restoration material for example by applying energy, for example with a laser, whereby the treatment can be any treatment such as material removal, material addition, polishing, coloring, texturing, and the like or combinations thereof. The system can support the processing of dental materials used in any type of restoration including but not limited to veneers, onlays, inlays, crowns, bridges, dentures, and implant abutments.

Figure 1:
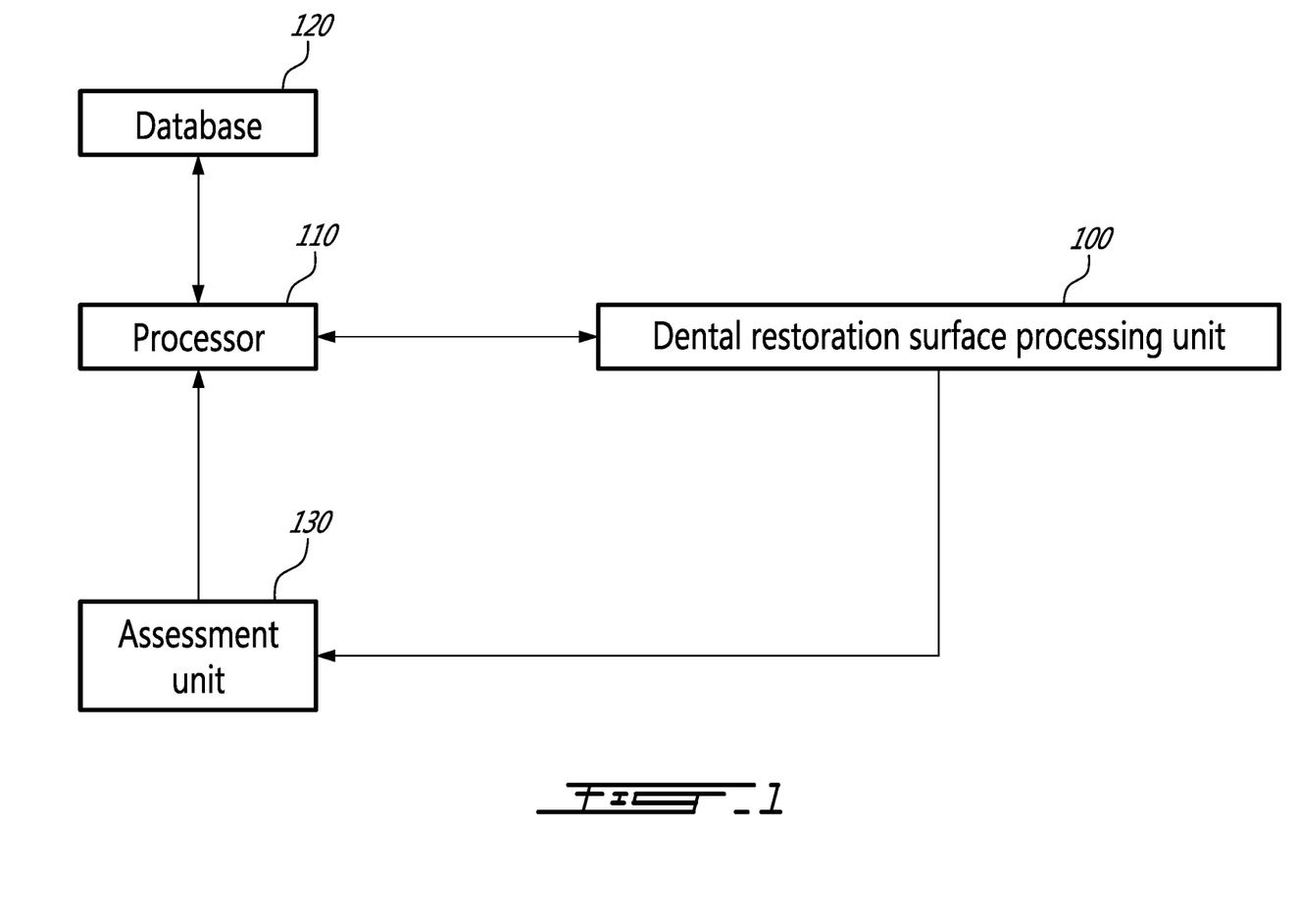
FIG. 1 is a schematic representation of a system of the invention.

With reference to FIG. 1, a high level schematic of the system is shown to comprise a dental restoration surface processing unit 100 for processing the dental restoration material according to a processing protocol, processor 110, a database 120, and, optionally, a dental restoration assessment unit 130 which may comprise sensors for measuring one or more assessment parameters selected from optical, mechanical, physical, geometric (such as macro or micro topography) or chemical data characterizing said dental restoration surface.

The dental material processing unit comprises tool or tools for processing the dental restoration material/surface. Such tools, used for the fabrication of dental prostheses are well known in the art and include but are not limited to, milling tools, polishing tools (abrasive), lasers (sintering, melting, ablation),sputtering tools, additive manufacturing tools, and the like. The choice of tools for the processing is a function of the type of material (or materials) that is used and the nature of the restoration.

Likewise many different types of materials are known in the art each having specific characteristics that can be exploited as a function of the type of prosthesis and the nature of the restoration. A non-limiting list of biocompatible dental material includes but is not limited to oxide ceramics, glass ceramics, porcelain, dental composites (polymer and ceramic), polymerizable polymers, glass ionomer cement, metal, and the like.

The processor 110 is configured to enable the implementation of the processing protocol. The processor is therefore connected to the dental restoration surface processing unit such as to control the tools/devices required to process the restoration material and to the database 120 comprising the protocols. Several control points may be required to manufacture the finished prosthesis: measuring and or analysing the material, positioning the material with respect to the treatment device, control of the duration and/or intensity of a treatment step, control of environmental conditions within the processing unit etc. The processor may also be designed to acquire optical, mechanical, physical, or chemical data from the dental material being treated as well as from the environment within the processing unit through assessment unit 130. The optical, mechanical, physical, or chemical data may then be stored in the database for further use as will be described in more details below. The system may also receive information collected directly or indirectly from a patient. For example an intra-oral scanner, an intra-oral 2D camera, an x-ray, or digital shade scanner may be connected to the processor and information received therefrom can be analyzed and used to build or modify a protocol.

Figure 2:
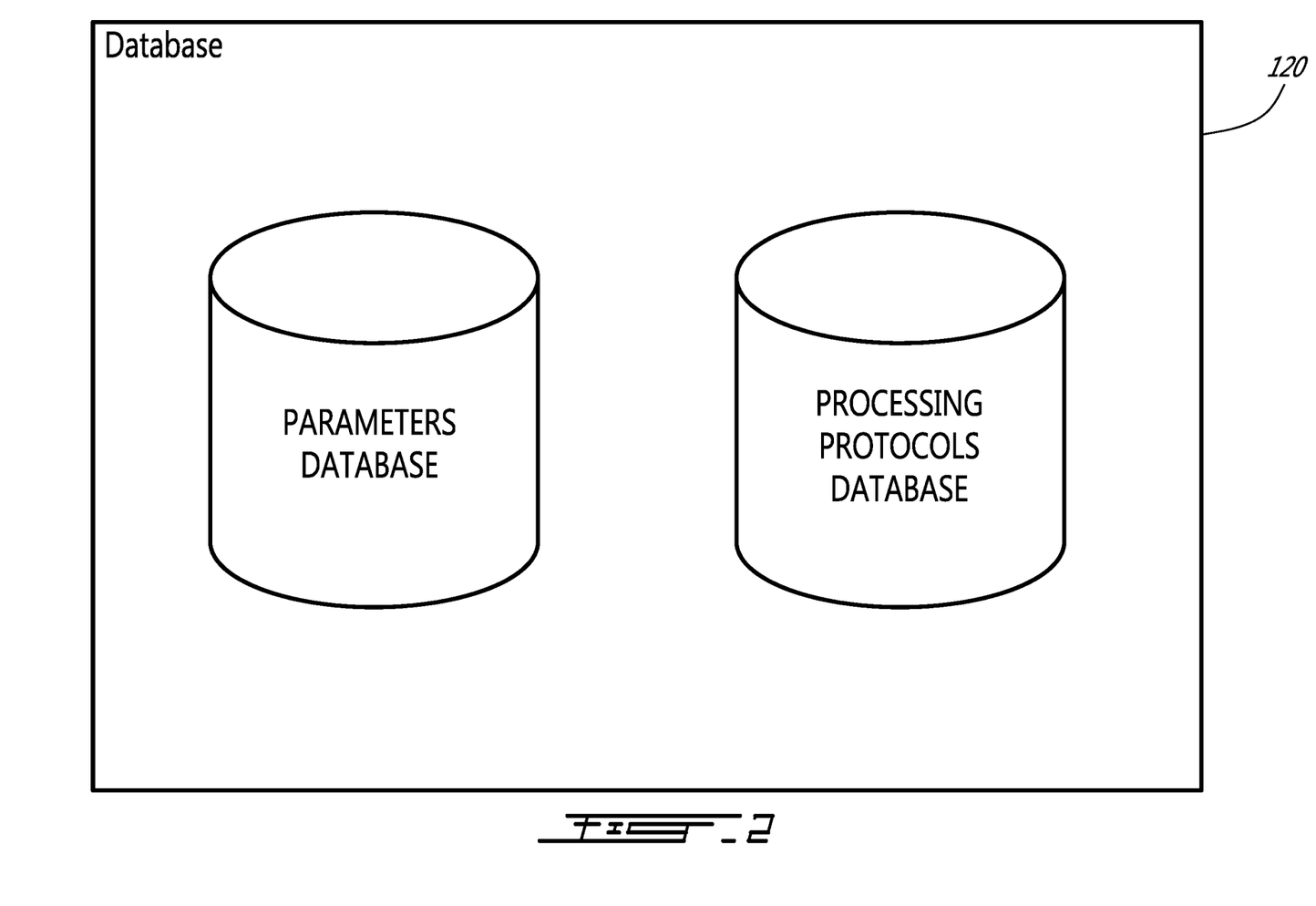
FIG. 2 is a schematic representation of a database of a system of the invention.
Figure 3:
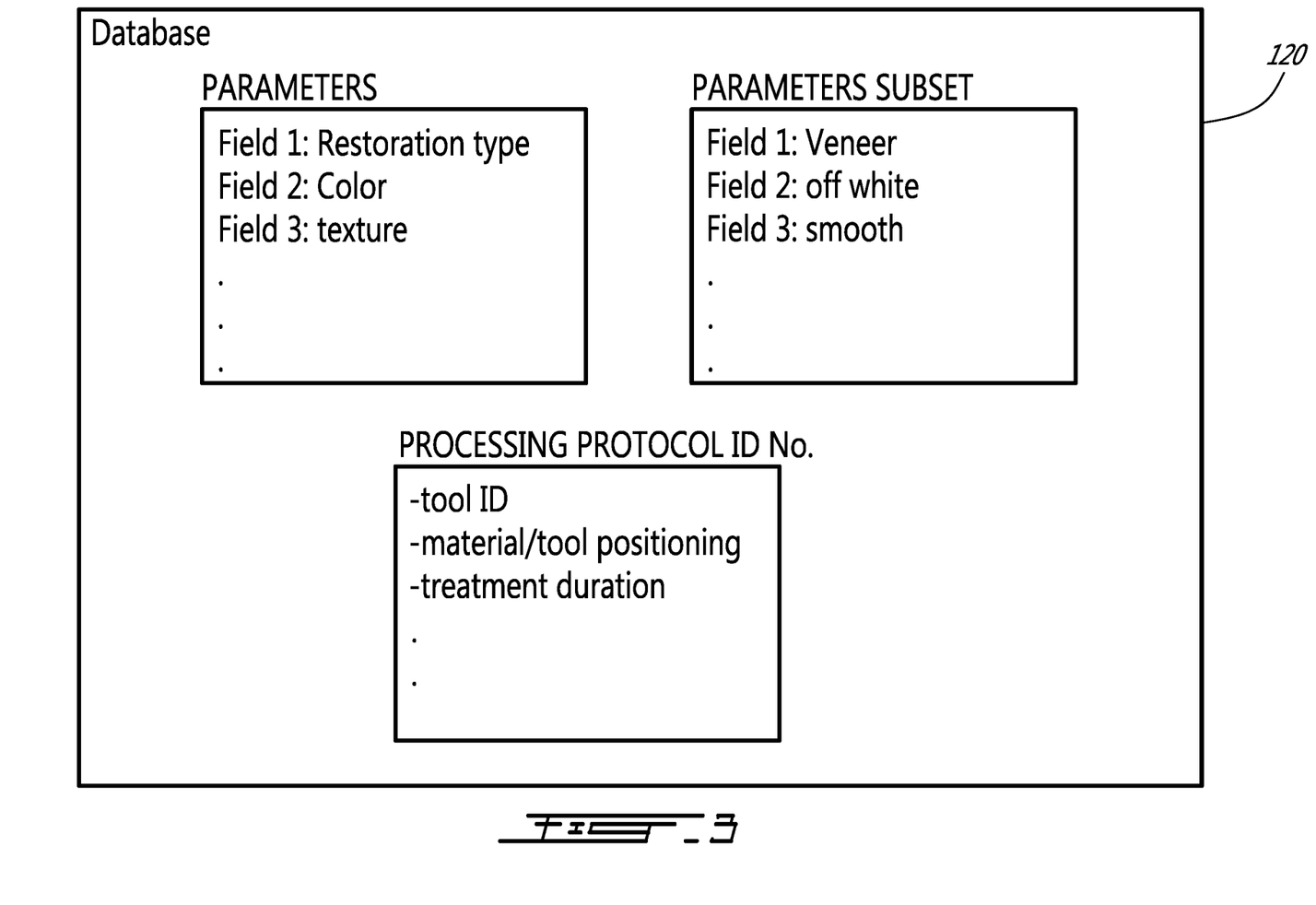
FIG. 3 is a schematic representation of another embodiment of a database of a system of the invention.

Referring now to FIGS. 2 and 3, database 120 may comprise a parameters database and a processing protocols database. An example of the database content description is provided in FIG. 3. In one aspect, the parameters database comprises a number of parameters fields containing information on the type of restoration, desired physical characteristics of the dental material, type of material etc. Upon selection of the parameters for a given restoration/processing a subset of parameters is created that determines the processing protocol to be used for processing the dental restoration material. For example a subset of parameters may comprise fields identifying the type of restoration (veneer, inlay etc.), the type of material (ceramic, composite etc.), and the desired physical characteristics of the finished prosthesis (color, texture, micro-structures for functional adaptation etc.). The database may further comprise a set of processing protocols, each one comprising the necessary information to enable a complete algorithmic processing treatment of the dental material or any part thereof based on the selected parameters. A processing protocol may therefore comprise information on the choice processing tool, the duration of a particular treatment, spatial positioning of the dental material relative to a treatment tool and any other information necessary to execute the processing treatment. The information contained in the protocol is relayed to the processor 110 to implement the processing steps within the dental restoration surface processing unit.

With regard to the type of information that a processing protocol may comprise the following provide additional examples: the outer surface shading may be directed at different anatomical parts of the teeth as for example blue or tones of blue in incisal direction on cusp or brown or tones of brown on the bottom part of the prosthesis. The processing protocol may also comprise information on the surface topography such as to generate fake cracks for example.

Polishing and in particular laser polishing of the inner surface may create structures that provide functionality to certain anatomical parts. For example specific polishing of the margin area to reduce the retention of bacteria near the gingival, specific micro-structure shape given to the cervical area in order to increase the watertight of the prosthesis on the stump to increase reliability, specific micro-structure shape applied to the dilation area in order to increase the retention of the prosthesis on the clinical situation, specific code engraving on the inner surface of the prosthesis for forensic identification or traceability purpose which could be automatically stored in the databases. It will be appreciated that functional processing of the surface may require specific shading to hide the functional substructure.

Thus the system of the invention and in particular when laser is used to process the prosthesis enable the creation of mechanical features like retention (undercut) or mechanical barrier ("3D ring") at a scale which is not accessible to a milling tool. Furthermore functional processing can generate a texture that provides a larger gluing surface by the creation of dedicated roughness for example.

It will be appreciated that functional processing can create structural features that lend themselves to the use of special cements designed with the proper granulometry and chemistry to exploit these features.

Figure 4:
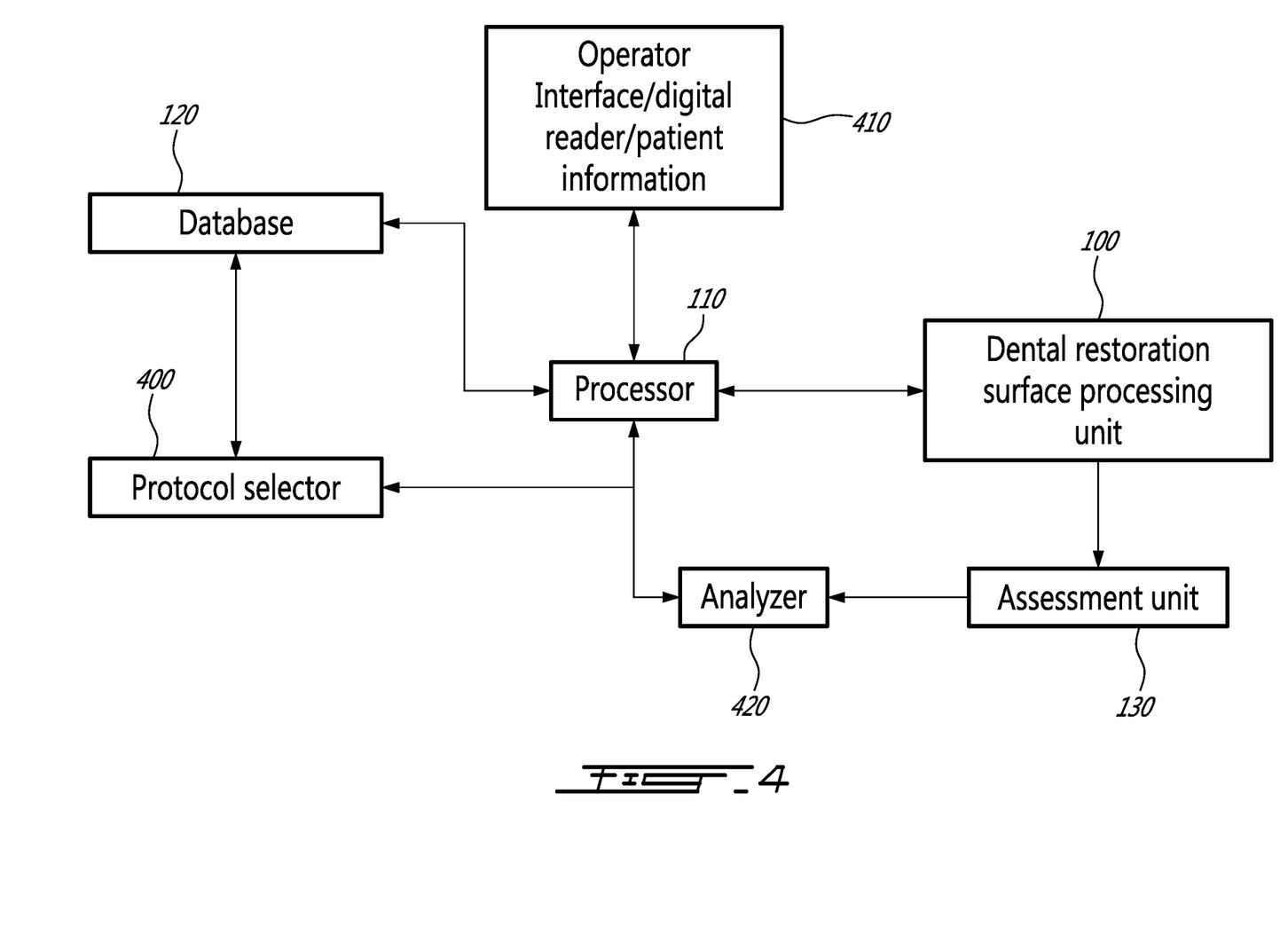
FIG. 4 is schematic representation of another embodiment of a system of the invention.

As described in FIG. 4, the determination of a protocol is effected by a protocol selector 400. Inputs may be received from a user interface 410 or from a digital reading of identification information on the dental material or the file of the patient or any other information identifier. For example a laser such as a nanosecond pulse laser can be used to engrave information on the prosthesis. The information provided to the protocol selector comprises information corresponding to parameters fields of the parameters database and allows a user or the digital input information to initiate the selection of a processing protocol.

Thus the protocol selector receives input from a user interface or digital reader/scanner to identify certain parameters associated with a desired finished prosthesis. For example a user may select a string of parameters available from the parameters database: "veneer/off-white/rough/ceramic". This string of parameter is then used by the protocol selector to determine the steps to be included in the processing protocol to achieve the desired result. It will be appreciated that the selection available to a user may be hierarchical such that a particular field selection may define and/or restrict the choices available for other fields. Alternatively, and as previously mentioned, the selection may be performed automatically by a digitized identification system (bar code, RFID). In the case where the information is provided digitally the system may be completely automated thereby reducing the risk of errors and increasing the efficiency.

Advantageously, in the system of the present invention, a processing protocol may be dynamically modified upon receiving input information from other parts of the system. By dynamically modified it is meant that the protocol is adjusted or modified during the processing of the dental material in response to the optical, mechanical, physical, or chemical modification of the material being treated. As will be appreciated, processing of the material may result in the production of artefacts. For example laser sintering is known to produce curling or delaminating. Thus in one embodiment, sensors 130 are integrated in the system to collect information on the optical, mechanical, physical, or chemical state of the dental material at any desired time during the processing. The detectors may be selected depending on the nature of the treatment and the nature of the information required. For example, cameras or spectrophotometers may be used for detecting color changes, ultrasounds may be used to assess the density, gas/chemical detectors to detect the evolution of gases, thermometers or infrared detectors to monitor the temperatures, reflective illumination microscope and laser surface scanners may be used to detect micro structure modifications.

Furthermore the system may comprise sensors to acquire information on the environment surrounding the material being processed. In this respect the temperature, pressure, humidity level and the like may be monitored by the sensors. The "environment" sensors provide a means for optimizing the processing to the surface. For example processing to modify the shading or material removal may be dependent on the temperature or pressure. Other aspects of the processing may also be improved by controlling the environment as for example by providing compressed air in a controlled manner to remove the plume and the re-deposition effect created by the processing (such as laser processing) of certain materials or creating vacuum to remove and treat residues and fumes created by the processing.

The information collected by the sensors is provided to an analyzer 420 which receives the measured optical, mechanical, physical, or chemical data and analyzes them to update the processing protocol in response thereto. The measurements data may be analyzed in a number of ways. For example, the data acquired by the sensors can be compared to pre-determined ranges for a particular type of measurements and the processing protocol may be adjusted when the measurements data fall outside the range. Data from the sensors may also be utilized as signals for initiating or terminating steps in the processing of the material. For example a particular step of the process may be initiated when the temperature within the processing unit or when reflection of light of a given frequency on the dental material reach predetermined values.

Figure 5:
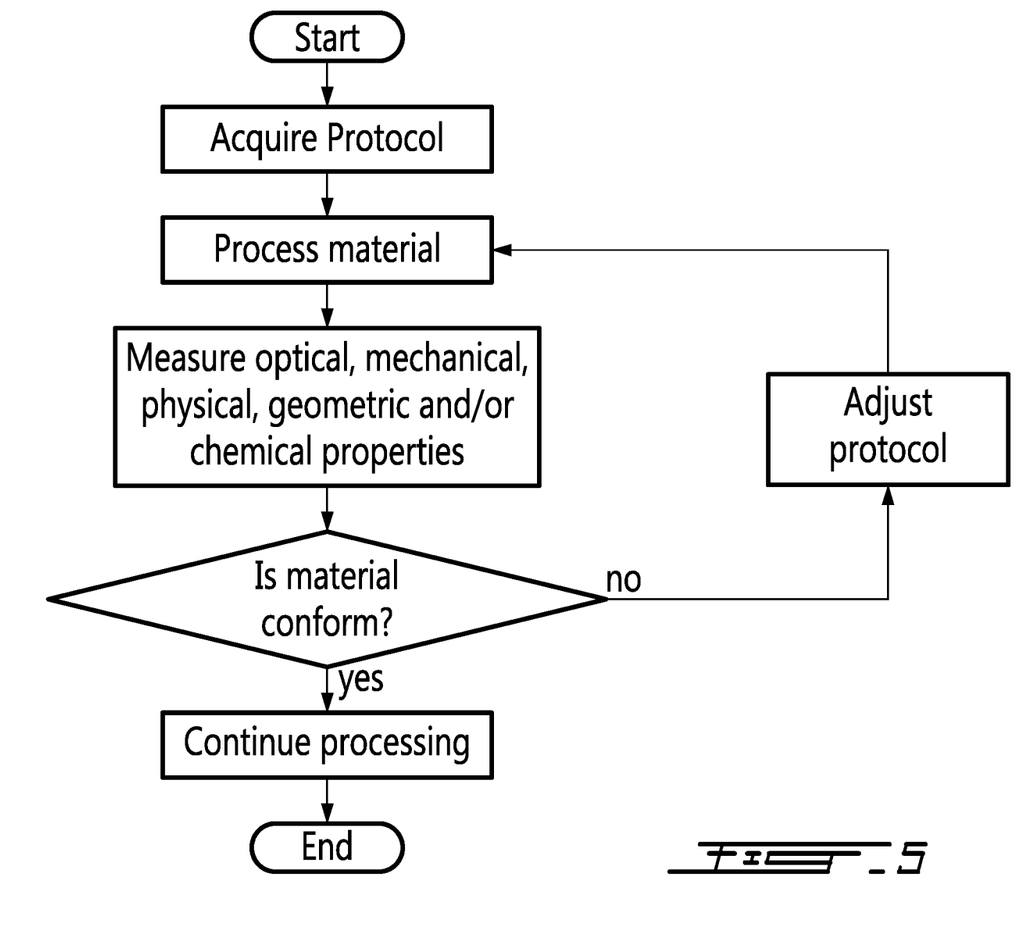
FIG. 5 is flow chart diagram of a method for processing dental material according to an embodiment of the invention.

FIG. 5 shows an example of a flow chart for a processing protocol adjustment wherein a protocol is first acquired by the processor to start a particular treatment. The material is then processed and either simultaneously or after any pre-determined time or point in the process, any number of optical, mechanical, physical, or chemical properties of the material or the environment within the processing unit are assessed. The data acquired from the sensors is then analyzed. If the material and/or the environment is in conformity then the treatment continues with the current processing protocol. If however the material or any part thereof and/or the environment is not in conformity then a protocol adjustment loop is initiated and further processing is performed with the adjusted protocol.

Thus a processing protocol may be dynamically created/adjusted based on input information. The process may be dictated by a combination of a predetermined protocol with a dynamically created/adjusted protocol.

Figure 6:
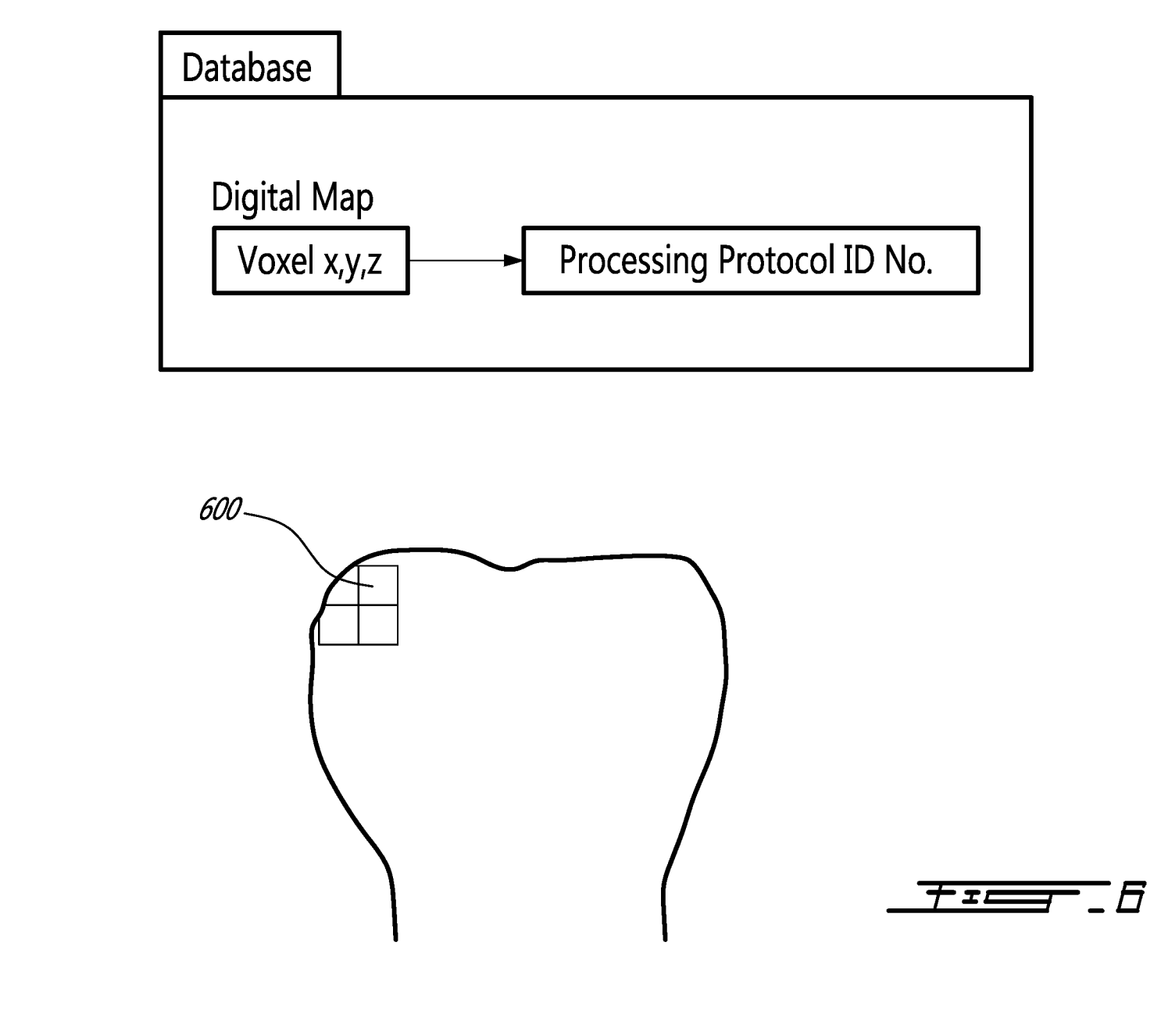
FIG. 6 is schematic representation of a digital map according to an embodiment of the invention.

The execution as well as the modification of a processing protocol with the system of the present invention is advantageously optimized by the use of a digital map corresponding to the spatial configuration of the material being treated such that the physical characteristics of each region or part of the material may be independently monitored and processed. Therefore it is possible to not only direct a particular treatment to the desired location on the material but also to associate a processing protocol with a given area or volume of the material. Each such region can be associated with a different protocol or a group of regions may be associated with a given protocol while another group of regions associated with a different protocol. Thus in one embodiment each pixel or voxel 600 (FIG. 6) of the digital map may be associated with a processing protocol that can take into account the local properties of the dental material and its response to treatments as measured by the sensors.

The digital map is stored in the database. It can be a pre-determined map or it can be acquired and built based on a design of a prosthesis or a scan of a tooth or teeth or a bore or an dental impression, or a combination of the above.

The digital map itself may be modified as a function of the treatment. For example the resolution of the map may depend on the resolving power of the tool being used for the processing. It will be appreciated that a laser beam offers a greater resolution than a polishing device using abrasive material. The modification of the digital map may also be a dynamical modification that follows the requirements of an evolving treatment.

It will be appreciated that the processing of the material may involve the use of a plurality of treatment techniques either simultaneously or in succession. Successive treatments may even be applied to the same area of a dental material either as part of a pre-determined protocol or as a result of a protocol adjustment in response to sensors measurements. Successive treatments with different tools may require different digital maps.

Figure 7:
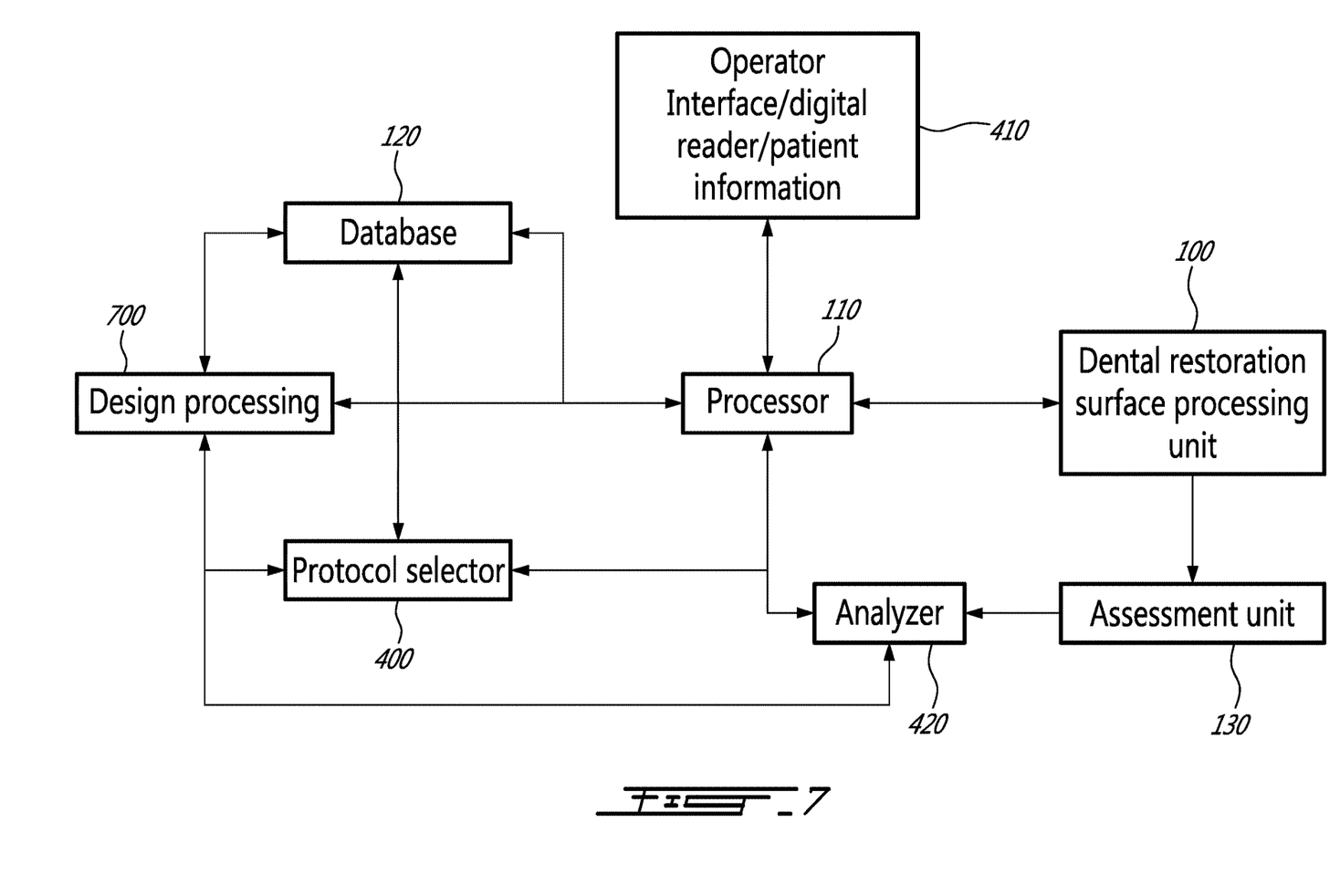
FIG. 7 is a schematic representation of a further embodiment of a system of the invention.
Figure 8:
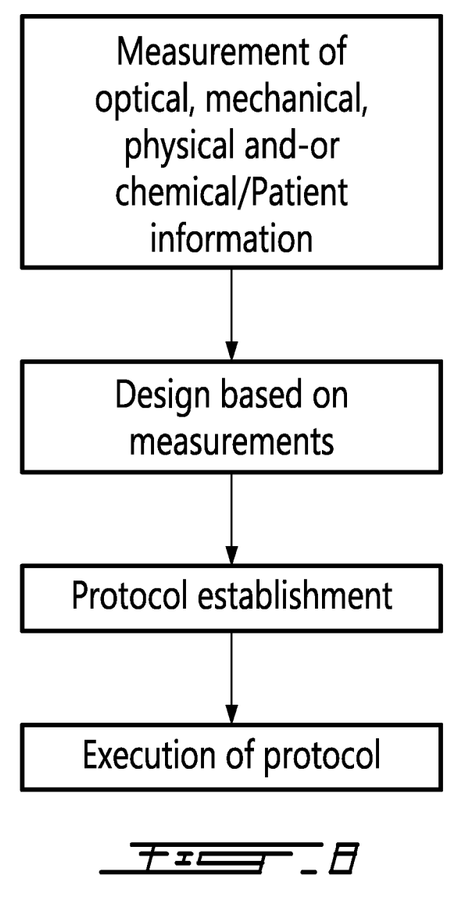
FIG. 8 is a flow chart diagram of a method for establishing a processing protocol based on input information.

In a further aspect of the invention the desired attributes of the final finished prosthesis may be designed and the design provided to the system to generate associated parameters. The parameters are then used to determine the processing protocol associated with the design. The design may be computer generated using CAD/CAM technologies. Alternatively, the processing protocol may comprise the necessary information to automatically design the prosthesis. In this respect a design database may be provided from which designs can be selected in accordance with treatment parameters. The processing protocol may also comprise instructions enabling a design processor 700 (FIG. 7) to generate a design based on inputs from a user or inputs automatically acquired by the system as shown on the flow chart of FIG. 8. Such inputs may comprise scans for teeth structures, optical, mechanical, physical, or chemical properties acquired by the sensors, patient information and the like. Advantageously, the input information may be selected to be specific for a particular type of restoration or a specific step of the dental material processing thereby avoiding acquisition of information that is not relevant to a particular design.

EXAMPLE 1

In one embodiment, a digital map of the material, which can be a partly finished prosthesis or a prosthesis in the finishing stages, is acquired. Then a user may select parameters (or the parameters may be automatically selected) for treatment such as for example laser polishing.

Type of restorations that are encompassed by the present examples without being limited to are veneers, onlays, inlays, crowns, bridges, dentures, and implant abutments. While the examples mostly discuss ceramic material other materials and particularly other materials amenable to treatment can be used.

The material can be described either automatically or through user inputs by attributes such as, morphology, thermal sensitivity properties, granularity, density etc.

The attributes are then associated with a digital 3D map thus creating the map of the initial optical, mechanical, physical, or chemical properties of the material. Then for each voxel of the map a desired custom surface properties is created (color, polishing, hardness). It will be appreciated that the map of the desired custom surface properties may be created by user inputs or by an automatic design based on a scan of adjacent structures or a combination of bath. The desired properties then determine the processing protocol. In the case of laser treatment such parameters as laser mode, wavelength, power, frequency, spot size, pulse duration, and the like are determined. The processing protocol is then activated by the processor and the proper sequence of steps are implemented to produce the desired effect.

The progress of the treatment can be monitored. With regard to the smoothness of the surface, the reflection/refraction of light on the surface can be monitored.

EXAMPLE 2

Finishing of a Prosthesis Using Laser

In one embodiment there is provided a method and apparatus for the laser finishing/polishing of dental material for making prosthesis and more specifically for the laser finishing/polishing of ceramic material.

It has been discovered that post-processing (finishing/polishing) of a ceramic prosthesis can be achieved with a laser using a processing protocol comprising laser parameters creating pre-determined, dynamically controlled, localized energy deposition. In the case of ceramic it has been found that by overlapping the focal spots of successive laser pulses it is possible to generate a surface having lower surface roughness and glazed finish with glossed surface having a high translucency. In one aspect two successive pulses can have overlapping areas of between about 50 and 90%. It will be appreciated that the extent of the overlap is dependent on the desired result. Without wishing to be bound by any theory, the overlapping of successive pulses allows a much finer control over the evolution of the physical state of the treated material thereby enabling a more controlled finish of the prosthesis.

Specific laser polishing parameters are established based on the material composition type and the initial surface condition as well as the desired optical, mechanical, physical, or chemical properties of the finished product. For ceramic and ceramic-like materials it has been found that the following ranges are preferred:

Laser wavelength: 1060 nm (while this is a preferred embodiment another wavelength in the infra-red range could be selected).

Pulse duration: 20-100 ns
Energy per pulse: 200-500 uJ
Pulse repetition rate: 41 kHz-266 kHz
Spot size 15-30 um
Pulse overlapping &: 50%-90%

Thus in one embodiment the processing steps may be as follows:

Create a rough geometry from a black of material (preform) leaving and excess of material (typically 50-100 micron) in the region to be polished herein after referred as the pre-form.

Determine laser trajectory and position of laser focal spots and/or material pre-form spatial positioning that allows the treatment of the surface to be polished with the predefined pulse overlap that correspond to the desired surface finish. The positioning of the laser pulse and the material can be done either sequentially or simultaneously and the laser pulse(s) can be synchronized with the positioning of the surface by taking into consideration parameters such as surface cooling, angle between laser beam and surface and the like.

Optionally, when polishing is completed, the resulting surface is evaluated with a sensor to qualitatively and/or quantitatively measure the results of the polishing. The sensors may be selected from but not limited to reflective light microscopy, electron microscopy, laser profiling, confocal microscopy, and any other technique known in the art for analyzing surface structures.

The data provided by the sensors can be processed and compared to predetermined desired values. The results of the comparison determine if additional processing is required and if yes, the results are used to adjust the laser treatment parameters and a new processing protocol is established.

Furthermore it has been discovered that the effect of the laser on the surface is sensitive to the angle between the laser beam and the surface at the point of treatment. For a restoration surface which presents a convex or flat shape the polishing can be accomplished by directing the laser beam at low angle of attack with respect to the surface to the desire spot to be polished. It has been surprisingly discovered that for ceramic material an angle of less than 20 degrees 16 will increase significantly the quality of the polishing. Therefore, the beam is displaced along the surface to be treated by keeping the beam angle of attack to a low value while covering the entire surface to be polished.

Contrary to mechanical abrasion techniques for polishing that require sturdy and bulky holders because of the pressure that is necessary to apply on the surface, the treatment of dental restoration surface with non-contact energy sources allow the use of very small and precise positioning means. Thus within the treating area the material is held by a holder that is part of the positioning unit for 3D manipulation of the dental material while allowing the energy source, such as laser energy, to reach its target without being obstructed. The system may further comprise a sensor such as visible light camera to measure the shade/color for providing data to evaluate and adjust the processing protocol.

EXAMPLE 3

Coloring of Dental Material

The methods of the present invention can also be applied to shading/coloring which can be accomplished by mean of controlling the elevation of the temperature on or below the surface of the dental restoration material, by thermally or chemically activating or changing dopants within or applied to the surface of the ceramic material. The laser pulse overlapping technique described above or the treatment of the surface with non-overlapping pulses, which can be applied repetitively to the surface or not, can be used to that effect. In the example of a localized controlled thermal change of a ceramic material, localized temperature elevation causes the crystalline transformation of the material. Shading/coloring is accomplish by controlling the amount of energy delivered to the material varying laser pulse characteristic such as pulse duration, wavelength, 17repetition rate, energy per pulse. In a specific embodiment, the temperature in a region of the surface may be elevated such that the laser pulse is only used to create a small necessary temperature increase to change shading/coloring. This temperature is material specific but could be the crystallization temperature for example.

Thus in one example there is provided system comprising a motion/positioning unit such as linear actuators, galvanometer in translation or in rotation by stepper motor, servo motors and the like capable of positioning the selected surface to be polished at precise location and orientation (x,y,z and yaw and roll) with respect to the laser.

Although the present invention has been described hereinabove by way of specific embodiments thereof, it can be modified, without departing from the spirit and nature of the subject invention as defined in the appended claims.

What is claimed is:

1. A system for post-processing a surface of a manufactured dental restoration to achieve at least one desired characteristic of an exterior of the dental restoration, the system comprising:
a dental restoration surface processing unit comprising at least one tool for post-processing the surface of the manufactured dental restoration;
a dental restoration assessment unit comprising at least one sensor for measuring at least one assessment parameter comprising data characterizing the surface of the manufactured dental restoration;
an analyzer receiving and analyzing said at least one assessment parameter;
a database comprising a processing parameters database comprising a plurality of processing parameters from which at least one treatment parameter is selected and a processing protocols database comprising a plurality of processing protocols;
a protocol selector configured to select one of said plurality of processing protocols based on the at least one desired characteristic of the exterior of the dental restoration and said at least one selected treatment parameter and wherein said at least one analyzed assessment parameter is used to adjust said selected processing protocol; and
a processor operationally coupled to said dental restoration surface processing unit to execute a post-processing of the surface of the manufactured dental restoration based on said selected processing protocol.

2. The system of claim 1, wherein said at least one assessment parameter is selected from optical data, mechanical data, physical data, chemical data, geometric data and combinations thereof.

3. The system of claim 1, wherein said at least one sensor is selected from reflective light microscopy, electron microscopy, laser profiling, confocal microscopy ad combinations thereof.

4. The system of claim 1, further comprising a parameters subsets database.

5. The system of claim 1, further comprising a user input port for entering parameters choices.

6. The system of claim 1, further comprising an input port for receiving dental information from a patient.

7. The system of claim 6, wherein said dental information is selected from a dental impression, a scan of a dental impression, an intraoral scan, an x-ray, a two dimensional digital image, a digital shade or color scan, and combinations thereof.

8. The system of claim 1, wherein said dental restoration surface processing unit comprises a positioning system for relative orienting of the surface and said at least one tool.

9. The system of claim 1, wherein said processor is also configured to control the environment within said dental restoration processing unit.

10. The system of claim 1, wherein said database further comprises a digital map of the surface.

11. The system of claim 10, wherein said digital map is a three dimensional map.

12. The system of claim 10, wherein said digital map comprises information about the surface selected from topography, surface finish, surface color, volume, chemical composition, physical composition, material composition, anatomical features and combinations thereof.

13. The system of claim 10, wherein said plurality of processing protocols, said at least one treatment parameter and said at least one assessment parameter are associated with coordinates of said digital map.

14. The system of claim 10, wherein said digital map is a dynamic map.

15. The system of claim 1, further comprising a design processor for generating a restoration design of the surface.

16. The system of claim 1, wherein said at least one assessment parameter is selected from temperature, pressure, humidity and combinations thereof.

17. The system of claim 1, wherein said at least one desired characteristic of an exterior of said surface comprises at least one of a shade, a surface accuracy, a surface resolution or a surface texture.

18. A method for post-processing a manufactured dental restoration comprising:
manufacturing the dental restoration comprising a surface to be treated;

determining at least one desired characteristic of an exterior of said surface;

measuring at least one assessment parameter of said surface;

selecting at least one processing protocol according to which said surface is to be treated to achieve said at least one desired characteristic of said exterior, wherein said at least one processing protocol is dynamically adjusted in response to said at least one measured assessment parameter; and post-processing said surface based on said at least one selected processing protocol.

19. The method of claim 18, wherein said at least one processing protocol by which said surface is to be treated comprises at least one act selected from polishing, texturing, shading, hardening, modifying translucency, creating functional features, and combinations thereof.

20. The method of claim 18, wherein said at least one assessment parameter is selected from an optical parameter, a mechanical parameter, a physical parameter, a chemical parameter, a geometric parameter and combinations thereof.

21. The method of claim 18, further comprising providing a digital map of said surface in a database.

22. The method of claim 21, wherein said digital map comprises at least one assessment parameter selected from an optical parameter, a mechanical parameter, a physical parameter, a chemical parameter, a geometric parameter and combination thereof of said surface.

23. The method of claim 21, wherein said digital map is associated with at least one corresponding said processing protocol.

24. The method of claim 18, further comprising generating a design protocol for designing said surface.

25. The method of claim 18, further comprising measuring at least one environmental parameter selected from temperature, humidity, pressure and combinations thereof.

26. The method of claim 18, wherein the dental restoration is manufactured from a ceramic dental restoration material and said processing comprises laser processing, wherein said at least one processing protocol comprises treating the surface of said ceramic dental restoration material with a plurality of laser pulses from a laser, each of said plurality of laser pulses having a focal spot area less than that of a total area of said surface and each of said plurality of laser pulses having a predetermined overlapping area with at least one previously applied laser pulse.

27. The method of claim 26, wherein said predetermined overlapping area is between about 50% and 90% of a previously applied said focal spot area of said plurality of laser pulses.

28. The method of claim 26, wherein each said laser pulse has an energy of between 200 and 400 nJ.

29. The method of claim 26, wherein said laser has a repetition rate of about 40 to 270 KHz.

30. The method of claim 26, wherein said laser processing is selected from surface finish and coloring.

31. The method of claim 18, wherein said surface is part of a prosthesis selected from veneers, onlays, inlays, crowns, bridges, dentures, and implant abutments.

32. The method of claim 18, wherein said at least one desired characteristic of an exterior of said surface comprises at least one of a shade, a surface accuracy, a surface resolution or a surface texture.

\* \* \* \* \*